US009974763B2

(12) United States Patent
Ben-Ari et al.

(10) Patent No.: US 9,974,763 B2
(45) Date of Patent: May 22, 2018

(54) MODULATORS OF INTRACELLULAR CHLORIDE CONCENTRATION FOR TREATING NEURODEGENERATIVE DISEASES WITH PARKINSONIAN SYNDROMES

(71) Applicants: B & A THERAPEUTICS, Marseilles (FR); CENTRE HOSPITALIER UNIVERSITAIRE DE NANTES, Nantes (FR); INSERM (INSTITUT NATIONAL DE LA SANTE ET DE LA RECHERCHE MEDICALE), Paris (FR); UNIVERSITE D'AIX-MARSEILLE, Marseilles (FR); UNIVERSITE DE NANTES, Nantes (FR)

(72) Inventors: Yehezkel Ben-Ari, La Ciotat (FR); Nathalie Dehorter, Bouguenais (FR); Philippe Damier, Vincennes (FR); Constance Hammond, La Ciotat (FR)

(73) Assignees: B&A THERAPEUTICS, Marseilles (FR); CENTRE HOSPITALIER UNIVERSITAIRE DE NANTES, Nantes (FR); INSERM (INSTITUT NATIONAL DE LA SANTE ET DE LA RECHERCHE MEDICALE), Paris (FR); UNIVERSITE D'AUX MARSEILLE, Marseilles (FR); UNIVERSITE DE NANTES, Nantes (FR)

( * ) Notice: Subject to any disclaimer, the term of this patent is extended or adjusted under 35 U.S.C. 154(b) by 0 days. days.

(21) Appl. No.: 14/894,621

(22) PCT Filed: May 28, 2014

(86) PCT No.: PCT/EP2014/061092
§ 371 (c)(1),
(2) Date: Nov. 30, 2015

(87) PCT Pub. No.: WO2014/191471
PCT Pub. Date: Dec. 4, 2014

(65) Prior Publication Data
US 2016/0106693 A1    Apr. 21, 2016

(30) Foreign Application Priority Data

May 31, 2013   (EP) ..................... 13170183

(51) Int. Cl.
*A61K 31/196* (2006.01)
*A61K 45/06* (2006.01)
*C12N 15/113* (2010.01)
*A61K 31/192* (2006.01)

(52) U.S. Cl.
CPC .......... *A61K 31/196* (2013.01); *A61K 31/192* (2013.01); *A61K 45/06* (2013.01); *C12N 15/1138* (2013.01)

(58) Field of Classification Search
CPC .... A61K 31/196; A61K 45/06; A61K 31/192; C12N 15/1138
See application file for complete search history.

(56) References Cited

U.S. PATENT DOCUMENTS

2013/0324503 A1*  12/2013  Payami ................ C12Q 1/6883
514/165

FOREIGN PATENT DOCUMENTS

WO        2006110187        10/2006
WO        2012/018635 A2    2/2012

OTHER PUBLICATIONS

Dehorter et al. "Subthalamic Lesion or Levodopa Treatment Rescues Giant GABAergic Currents of PINK1-Deficient Striatum", (2012) J Neurosc. 32(50)18047-18053.
Beurrier et al., "Preservation of the direct and indirect pathways in an in vitro preparation of the mouse basal ganglia", (2006) Neuroscience 140:77-86.
Cossart et al., "Distribution of spontaneous currents along the somato-dendritic axis of rat hippocampal CA1 pyramidal neurons", Neuroscience, vol. 99, No. 4, pp. 593-603, (2000).
Dehorter et al., "Dopamine-Deprived Striatal GABAergic Interneurons Burst and Generate Repetitive Gigantic IPSCs in Medium Spiny Neurons", Jun. 17, 2009, The Journal of Neuroscience, 29(24):7776-7787.
International Search Report dated Sep. 9, 2014, in corresponding PCT Application.
Ryuta Koyama et al.: "GABAergic excitation after febrile seizures induces ectopic granule cells and adult epilepsy". Nature Medicine. vol. 18. No. 8, Jul. 15, 2012 (Jul. 15, 2012). pp. 1271-1278. XP055135835.
Brooks B. Pond et al.: "Chloride transport inhibitors influence recovery from oxygen-glucose deprivation-induced cellular injury in adult hippocampus", Neuropharmacology, vol. 47, No. 2, Aug. 1, 2004 (Aug. 1, 2004), pp. 253-262, XP055080292.

* cited by examiner

*Primary Examiner* — Sarah Pihonak
*Assistant Examiner* — Jason Deck
(74) *Attorney, Agent, or Firm* — Young & Thompson

(57) ABSTRACT

A composition for treating Neurodegenerative Diseases with Parkinsonian Syndromes in a subject in need thereof, wherein the composition includes an effective amount of a modulator of a chloride transporter.

11 Claims, 4 Drawing Sheets

MODULATORS OF INTRACELLULAR CHLORIDE CONCENTRATION FOR TREATING NEURODEGENERATIVE DISEASES WITH PARKINSONIAN SYNDROMES

FIELD OF INVENTION

The present invention relates to the treatment of neurodegenerative diseases with Parkinsonian Syndromes. More specifically, the present invention relates to a method for treating neurodegenerative diseases with Parkinsonian Syndromes in a subject in need thereof, wherein said method comprises modulating the intracellular level of chloride, such as, for example, by administering to the subject a modulator of chloride transporter.

BACKGROUND OF INVENTION

Neurodegenerative diseases with Parkinsonian Syndromes are disorders affecting the central nervous system and that are associated with akinesia and several other neurological disorders. The proportion of affected persons is about 0.3% of the whole population in industrialized countries.

Neurodegenerative diseases with Parkinsonian Syndromes usually affect people over the age of 50 except for a person suffering from an early-onset variant. Early symptoms of neurodegenerative diseases with Parkinsonian Syndromes are subtle and occur gradually. The primary symptoms of these disorders are: tremor or trembling in hands, arms, legs, jaw, and face; rigidity or stiffness of the limbs and trunk; bradykinesia, or slowness of movement, and postural instability, or impaired balance and coordination. Other symptoms may include depression and other emotional changes; difficulty in swallowing, chewing, and speaking; urinary problems or constipation; skin problems; and sleep disruptions. As these symptoms become more pronounced, patients may have difficulty walking, talking or completing other tasks.

Neurodegenerative diseases with Parkinsonian Syndromes such as Parkinson Disease (PD) comprise motor symptoms and non-motor symptoms.

Non-motor symptoms may include autonomic dysfunction, cognitive (impairment of cognitive and executive performances) and behavioral problems leading sometimes to dementia, and sensory, sleep and emotional problems (mostly depression). Treatment of these non-motor symptoms is not yet standardized although some drugs have been proposed such as antidepressant drugs (depression), clozapine (illusions, hallucinations), cholinesterase inhibitors (dementia treatment) and modafinil (sleep problems treatment).

The motor symptoms of degenerative disorders involving the dopaminergic system such as PD are collectively called "Parkinsonian Syndromes". Motor symptoms include, without limitation, bradykinesia, tremor at rest, rigidity or stiffness, shaking, slowness of movement and postural instability. Idiopathic Parkinson Disease is the most common cause of Parkinsonian Syndrome (about 65%). Other causes include, without limitation, Progressive Supranuclear Palsy, Multiple System Atrophy, Corticobasal Degeneration and Lewy Body Dementia, Wilson's disease.

Neurodegenerative diseases with Parkinsonian Syndromes are characterized by the loss of pigmented dopaminergic neurons in the Substantia Nigra of the mesencephalon leading to the absence of dopamine in the striatum and other basal ganglia. This in turn leads to aberrant enhanced neuronal activity in the striatum and basal ganglia, which produces the clinical symptoms.

At present there is no cure for neurodegenerative diseases with Parkinsonian Syndromes, but a variety of medications provide dramatic relief from the symptoms. Usually, patients are given Levodopa combined with carbidopa. Carbidopa delays conversion of Levodopa into dopamine until it reaches the brain. Nerve cells can use Levodopa to produce dopamine and replenish the brain's dwindling supply. Although Levodopa helps three-quarters parkinsonian patients, not all symptoms respond equally to the drug. Bradykinesia and rigidity respond best, while tremor may be marginally reduced. Problems with balance and other symptoms may not be alleviated at all.

Anticholinergics may help control tremor and rigidity. Other drugs, such as, bromocriptine, pramipexole, and ropinirole, mimic the role of dopamine in the brain, causing the neurons to react as they would to dopamine. An antiviral drug, amantadine, also appears to reduce symptoms. In May 2006, the FDA approved rasagiline (AZILECT®) to be used along with Levodopa for patients with advanced neurodegenerative diseases with Parkinsonian Syndromes or as a single-drug treatment for early neurodegenerative diseases with Parkinsonian Syndromes. A surgical treatment (i.e. deep brain stimulation applied to the sub-thalamic nucleus) is another recent option that can be considered in some PD patients. The treatment may act through a beneficial modulation of abnormal neural activities induced by the lack of brain dopamine.

In physiological conditions, the output neurons of the striatum, the Medium Spiny Neurons (MSNs) that comprises the vast majority of the neuronal population (over 95%) are inactive at rest as they have a much hyperpolarized membrane potential. They respond to synchronized cortical afferent activities only. This enables the motor cortex to generate striatal patterns needed for targeted movements. In neurodegenerative diseases with Parkinsonian Syndromes, the striatum is highly active, thereby perturbing the targeted movements' organization.

This hyperactivity was observed in mouse models of PD and is characterized by the generation of Giant GABAergic network driven Currents (GGCs) by MSNs of the Striatum (Dehorter et al. 2012; Dehorter et al., 2009). The causes of the dysfunction of these GABAergic signals are unclear but a link has been established with intracellular levels of chloride. Modulating intracellular levels of chloride may thus be a promising target for treating neurodegenerative diseases with Parkinsonian Syndromes.

The Applicant surprisingly showed that the use of antagonists of chloride co-transporters blocked aberrant GABAergic activity in the Striatum of a mouse model of PD as compared to the wild-type situation. Moreover, the Applicant showed in a clinical study that the use of antagonists of chloride co-transporters decreased the Parkinsonian Syndromes symptoms. The present invention thus relates to the use of a modulator of intracellular chloride level for treating neurodegenerative diseases with Parkinsonian Syndromes in a subject in need thereof.

SUMMARY

One object of the invention is a composition for use in the treatment of a neurodegenerative disease with Parkinsonian syndromes in a subject in need thereof, wherein said composition comprises an effective amount of a modulator of a chloride transporter, wherein said modulator is an inhibitor of a transporter involved in the importation of chloride into neurons.

In one embodiment of the invention, said inhibitor is an inhibitor of the activity of a transporter involved in the importation of chloride into neurons.

In another embodiment of the invention, said inhibitor is an inhibitor of the expression of a transporter involved in the importation of chloride into neurons, comprising siRNAs, shRNAs, microRNAs, antisense oligonucleotide, ribozymes DNAzymes, modified or synthetic DNA or RNA degradation-resistant polynucleosides amides, peptide nucleic acids (PNAs), locked nucleic acids (LNAs), other nucleobase-containing polymers, or aptamers of a chloride transporter involved in the importation of chloride into neurons.

In another embodiment of the invention, said transporter involved in the importation of chloride into neurons is NKCC, preferably NKCC1.

In another embodiment of the invention, said inhibitor of NKCC is a NKCC1 inhibitor.

In another embodiment of the invention, the inhibitor of NKCC is selected from the group comprising bumetanide, furosemide, ethacrynic acid, torsemide, azosemide, muzolimine, piretanide, tripamide and the like; thiazide and thiazide-like diuretics, such as bendroflumethiazide, benzthiazide, chlorothiazide, hydrochlorothiazide, hydroflumethiazide, methylclothiazide, polythiazide, trichlormethiazide, chlorthalidone, indapamide, metolazone and quinethazone; analogs, functional derivatives and/or prodrugs thereof.

In another embodiment of the invention, the composition further comprises one or more active agent(s) for treating Parkinsonian Syndromes and/or side effects of said active agent(s).

In another embodiment of the invention, the composition wherein a therapeutically effective amount of the composition is to be administered prior to, concurrent to, or subsequent to other active agent(s) for treating Parkinsonian Syndromes and/or side effects of said active agent(s).

In another embodiment of the invention, said neurodegenerative disease with Parkinsonian Syndromes is a Parkinson's disease, progressive supranuclear palsy, multiple system atrophy, corticobasal degeneration or a Lewy body dementia.

In another embodiment of the invention, the subject is at risk of developing a neurodegenerative disease with Parkinsonian Syndromes.

In another embodiment of the invention, the subject is diagnosed with a neurodegenerative disease with Parkinsonian Syndromes.

In another embodiment of the invention, the subject presents a genetic predisposition to a neurodegenerative disease with Parkinsonian Syndromes, preferably a mutation of the PARK6-gene.

In another embodiment of the invention, the subject is affected, preferably diagnosed, with an early-onset variant of PD, more preferably an autosomal recessive PARK6-linked Parkinsonism.

DEFINITIONS

In the present invention, the following terms have the following meanings:

"Neurodegenerative diseases with Parkinsonian Syndromes" or "Parkinson's disease" refer to a neurodegenerative disease leading to a vast number of motor symptoms which are usually associated with degenerative disorders involving the dopaminergic system such as Parkinson's disease. Symptoms of a parkinsonian syndrome may include, without limitation, tremor at rest; akinesia and rigidity, such as, for example, slowness of movements, amimia, micrographia, loss of arm swing, difficulties in walking, sensation of stiffness; joint pain, dystonia, swallowing disorders, abnormal tiredness, trembling sensation, bradykinesia, action tremor, tremors, dysarthria, dysautonomia, dysphagia, dystonia, eye apraxia, limb apraxia, myoclonus, oculomotor tremors, night tremor, gait and posture impairment, sleep disorders.

"Treatment" refers to both therapeutic treatment and prophylactic or preventative measures; wherein the object is to prevent or slow down (lessen) the targeted pathologic condition or disorder. Those in need of treatment include those already with the neurodegenerative disease with Parkinsonian Syndromes as well as those prone to have the neurodegenerative disease with Parkinsonian Syndromes or those in whom the neurodegenerative disease with Parkinsonian Syndromes is to be prevented. A subject or mammal is successfully "treated" for a degenerative disease with Parkinsonian Syndromes if, after receiving a therapeutic amount of a composition according to the invention, the patient shows observable and/or measurable reduction in or absence of one or more of the following: reduction in the number of pathogenic cells; reduction in the percent of total cells that are pathogenic; and/or relief to some extent, one or more of the symptoms associated with the neurodegenerative diseases with Parkinsonian Syndromes; reduced morbidity and mortality, and improvement in quality of life issues. The above parameters for assessing successful treatment and improvement in the disease are readily measurable by routine procedures familiar to a physician.

"Therapeutically effective amount" refers to the level or amount of agent that is aimed at, without causing significant negative or adverse side effects to the target, (1) delaying or preventing the onset of neurodegenerative diseases with Parkinsonian Syndromes; (2) slowing down or stopping the progression, aggravation, or deterioration of one or more symptoms of neurodegenerative diseases with Parkinsonian Syndromes; (3) bringing about ameliorations of the symptoms of neurodegenerative diseases with Parkinsonian Syndromes; (4) reducing the severity or incidence of neurodegenerative diseases with Parkinsonian Syndromes; or (5) curing neurodegenerative diseases with Parkinsonian Syndromes. An effective amount may be administered prior to the onset of neurodegenerative diseases with Parkinsonian Syndromes, for a prophylactic or preventive action. Alternatively or additionally, the effective amount may be administered after initiation of neurodegenerative diseases with Parkinsonian Syndromes, for a therapeutic action.

"Early stage of the disease" means during the first years after the diagnosis of said disease, before the occurrence of motor fluctuations. Depending of disease severity in an individual patient or disease subtype, the term "early stage of the disease" can thus mean several years of disease duration. In one embodiment, the term "early stage of the disease" means the first year, the first two, three, four, five, six, seven, eight, nine or ten years after the diagnosis of the disease.

"Subject" refers to a mammal, preferably a human.

"Modulator" refers to a compound that modulates intracellular chloride level. Preferably, a modulator is a compound whose administration leads to a decrease of intracellular chloride concentration. The said modulator may act on the expression, protein expression and/or the trafficking and/or on the activity of a chloride transporter.

"Selective modulator" refers to a selective inhibitor and a selective activator.

"Inhibitor" refers to refers to a natural or synthetic compound that has a biological effect to inhibit or significantly reduce or down-regulate the expression of a gene and/or a protein or that has a biological effect to inhibit or significantly reduce the biological activity of a protein. Consequently, "a NKCC inhibitor" refers to a natural or synthetic compound that has a biological effect to inhibit or significantly reduce or down-regulate the expression of the gene encoding for NKCC and/or the expression of the NKCC protein and/or the biological activity of NKCC.

"Selective inhibitor" refers to that the affinity of the inhibitor for the chloride transporter for instance NKCC is at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than the affinity for the other chloride transporters in particular KCC2.

"Activator" refers to a natural or synthetic compound which binds to the protein and stimulates the expression of a gene and/or a protein or that has a biological effect to stimulate the biological activity of a protein. Consequently, "a KCC activator" refers to a natural or synthetic compound that has a biological effect to stimulate the expression of the gene encoding for KCC and/or the expression of the KCC protein and/or the biological activity of KCC. The activator usually mimics the action of a natural activator that binds to the transcription factor.

"Selective activator" refers to that the affinity of the activator for the chloride transporter for instance KCC2 is at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than the affinity for the other chloride transporters such as NKCC1.

"About": preceding a figure means plus or less 10% of the value of said figure.

"Analog" refers broadly to the modification or substitution of one or more chemical moieties on a parent compound and may include functional derivatives, positional isomers, tautomers, zwitterions, enantiomers, diastereomers, racemates, isosteres or stereochemical mixtures thereof "Functional derivative" refers to a compound which possesses the capacity to modulate the concentration of chloride into neurons (inhibits the importation or activates the outflow of chloride).

"Pharmaceutically acceptable" refers to compounds and compositions which may be administered to mammals without undue toxicity. Accordingly, a "Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like.

For human administration, preparations should meet sterility, pyrogenicity, and general safety and purity standards as required by FDA Office of Biologics standards.

DETAILED DESCRIPTION

This invention relates to a composition comprising a modulator of intracellular chloride concentration for treating neurodegenerative diseases with Parkinsonian Syndromes.

According to an embodiment, the modulator of intracellular chloride is a modulator of a chloride transporter.

In one embodiment of the invention, the modulator of intracellular chloride concentration is a selective modulator of a chloride transporter.

According to one embodiment, the modulator of a chloride transporter inhibits the importation of chloride into neurons, preferably through the inhibition of transporters involved in the importation of chloride into neurons.

The inhibition of chloride importation can be determined by the skilled artisan and is well known in the state of the art. Example 1 describes in particular electrophysiological studies comprising the measurements (amplitudes and frequencies) of giant GABAergic currents.

In another embodiment of the invention, said modulator is a selective inhibitor of the protein and/or gene expression of a transporter involved in the importation of chloride into neurons.

Examples of transporters involved in the importation of chloride into neurons include, but are not limited to NKCC (wherein NKCC stands for "Na—K—Cl co-transporter"), such as for example, NKCC1. In one embodiment, the modulator of a chloride transporter is thus an inhibitor of NKCC, preferably NKCC1.

In one embodiment of the invention, the inhibitor of a chloride transporter inhibits the expression of said chloride transporter. Examples of inhibitors of the expression of a chloride transporter include, but are not limited to, siRNAs, shRNAs, antisense oligonucleotide, ribozymes, microRNAs, DNAzymes, modified or synthetic DNA or RNA degradation-resistant polynucleosides amides, peptide nucleic acids (PNAs), locked nucleic acids (LNAs), other nucleobase-containing polymers, or aptamers of a chloride transporter.

In another embodiment, the inhibitor of a chloride transporter inhibits the trafficking and/or the expression at the membrane of the chloride transporter.

In another embodiment, the inhibitor of a chloride transporter inhibits the activity of the chloride transporter. Examples of such inhibitors include, but are not limited to, antibodies, small molecules, minibodies, diabodies, or fragments thereof binding to the chloride transporter, and antagonists of the chloride transporter.

The activity of the chloride transporter can be measured by the skilled artisan and is well known in the state of the art. For example, the measurement of $^{86}$Rb flux can be determined in cells expressing or transfected with NKCC as described in Isenring et al 1998 JBC 273: 11295-11301.

In one embodiment, the inhibitor of the invention may consist in an antibody directed against a transporter involved in the importation of chloride into neurons.

Antibodies directed against said transporter can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against said transporter can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g. U.S. Pat. No. 4,946,778) can be adapted to produce anti-modulator, or anti-modulator ligands single chain antibodies. Chloride transporter inhibitor useful in practicing the present invention also include anti-modulator, or anti-modulator ligands antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to said transporter.

In another embodiment, the inhibitor of the invention can include isomers, tautomers, zwitterions, enantiomers, diastereomers, racemates, or stereochemical mixtures thereof. Inhibitors of the present invention can also comprise isosteres.

The term "isosteres" as used herein broadly refers to elements, functional groups, substituents, molecules, or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Other physical properties that isosteric compounds usually share include boiling point, density, viscosity, and thermal conductivity. However, certain properties are usually different: dipolar moments, polarity, polarization, size, and shape since the external orbitals may be hybridized differently.

The term "isomers" as used herein refers broadly to compounds having the same number and kind of atoms, and hence the same molecular weight, but differing with respect to the arrangement or configuration of the atoms in space. Additionally, the term "isomers" includes stereoisomers and geometric isomers. The terms "stereoisomer" or "optical isomer" as used herein refer to a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure can exist in some of the compounds of the present invention, which may give rise to stereoisomerism, the invention contemplates stereoisomers and mixtures thereof. The compounds of the present invention and their salts can include asymmetric carbon atoms and may therefore exist as single stereoisomers, racemates, and as mixtures of enantiomers and diastereomers. Typically, such compounds will be prepared as a racemic mixture. Such compounds can also be prepared or isolated as pure stereoisomers, i.e., as individual enantiomers or diastereomers, or as stereoisomer-enriched mixtures. Tautomers are readily inter-convertible constitutional isomers and there is a change in connectivity of a ligand, as in the keto and enol forms of ethyl acetoacetate (including tautomers of any said compounds.) Zwitterions are inner salts or dipolar compounds possessing acidic and basic groups in the same molecule. At neutral pH, the cation and anion of most zwitterions are equally ionized.

In one embodiment of the invention, said selective inhibitor interacts directly with the chloride transporter.

In one embodiment, said selective inhibitor is an antagonist of a chloride transporter importing chloride into neurons.

Examples of such inhibitors include, but are not limited to, NKCC inhibitor such as for example, NKCC antagonists. In one embodiment, the modulator is an antagonist of NKCC1. In one embodiment, the modulator is a specific antagonist of NKCC1.

In one embodiment of the invention, the inhibitor of a chloride transporter is an inhibitor of NKCC1, such as, for example, a diuretic (such as, for example, a loop diuretic); or a NKKC1 antagonist. In another embodiment, the modulator of a chloride transporter is a selective inhibitor of NKCC, preferably of NKCC1.

A "loop diuretic" as used herein refers to diuretics that act at the ascending loop of Henle in the kidney. These diuretics act specifically on NKCC co-transporters.

In one embodiment of the invention, the selective inhibitor decreasing the gene and/or protein expression and/or activity of the chloride co-transporter NKCC1, has a low affinity for KCC2.

In one embodiment of the invention, the selective inhibitor of the chloride transporter has an affinity for KCC2 inferior than $10^{-7}$ M, preferably $10^{-6}$ M, more preferably less than $10^{-5}$ M.

In another embodiment of the invention, the selective inhibitor of the chloride transporter has an affinity at least much higher to NKCC1 than to KCC2 (of at least 2 orders of magnitude, preferably of at least 4 orders of magnitude, more preferably of at least 5 orders of magnitude and most preferably of at least 6 orders of magnitude higher binding constant (at least $10^{-9}$, preferably more than $10^{-10}$).

In another embodiment of the invention, the selective inhibitor of the chloride transporter does not bind to KCC2 at all.

In one embodiment of the invention, the selective inhibitor of the chloride transporter refers to a molecule that has an affinity for the NKCC1 at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than its affinity for any one of other isoforms of NKCC transporters comprising NKCC2, KCC transporters comprising KCC1, KCC2, KCC3, KCC4, other transporter chloride including in a non-limiting list: Cl$^-$HCO3$^-$ transporter.

Examples of inhibitors of chloride transporter, preferably NKCC1, include but are not limited to bumetanide, furosemide, ethacrynic acid, torsemide, azosemide, muzolimine, piretanide, tripamide and analogs, functional derivatives and prodrugs of such compounds; thiazide and thiazide-like diuretics, such as bendroflumethiazide, benzthiazide, chlorothiazide, hydrochlorothiazide, hydroflumethiazide, methylclothiazide, polythiazide, trichlormethiazide, chlorthalidone, indapamide, metolazone and quinethazone; and analogs and functional derivatives of such compounds.

Examples of analogs of bumetanide include, but are not limited to, bumetanide aldehyde, bumetanide dibenzylamide, bumetanide diethylamide, bumetanide morpholinoethyl ester, bumetanide 3-(dimethylaminopropyl) ester, bumetanide N,Ndiethylglycolamide ester, bumetanide dimethylglycolamide ester, bumetanide pivaxetil ester, bumetanide methoxy(polyethyleneoxy)$_{n-1}$-ethyl ester, bumetanide benzyltrimethylammonium salt, bumetanide cetyltrimethylammonium salt, pivaloyloxymethyl ester of bumetanide, methyl ester of bumetanide, N,N-dimethylaminoethyl ester of bumetanide, bumetamide [—(C═O)—SH] thioacid, bumetanide S-methyl thioester, bumetanide S-cyanotnethyl thioester, bumetanide S-ethyl thioester, bumetanide S-isoamyl thioester, bumetanide S-octyl thioester, bumetanide S-benzyl thioester, bumetanide S-(morpholinoethyl)thioester, bumetanide S-[3-(dimethylaminopropyl)]thioester, bumetanide S—(N,N-diethylglycolamido)thioester, bumetanide S—(N,N-dimethylglycolamido)thioester, bumetanide S-pivaxetil thioester, bumetanide S-propaxetil thioester, bumetanide 5-[methoxyipolyethyleneoxy)$_{n-1}$-ethyl]thioester, bumetanide [—(C═O)—S$^-$]benzyl-trimethylammonium thioacid salt and bumetanide [—(C═O)—S1 cetyltrimethylammonium thioacid salt; metast-able bumetanide thioacid, bumetanide thioaldehyde, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl)thioester, bumetanide O-[3-(dimethylaminopropyl)J thioester, bumetanide O—(N,N-diethylglycolamido)thioester, bumetanide O-pivaxetil thioester, bumetanide O-propaxetil thioester, bumetanide O-[methoxy(poryethyleneoxy)$_{n-1}$ ethyl]thioester, bumetanide [—(C═S)—O$^-$]benzyltrimemyl-ammonium thioacid salt and bumetanide [—(C═S)—O$^-$]cetyltrimethylammonium thioacid salt.

Examples of analogs of furosemide include, but are not limited to: furosemide aldehyde, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethylammonium salt, furosemide cetyltrimethylammonium salt, furosemide N,N-dimethylglycolamide ester, furosemide methoxy(polyethyleneoxy)$_{n-1}$-ethyl ester, furosemide pivaxetil ester, furosemide propaxetil ester, furosemide benzyltrimethylammonium acid salt and furosemide cetyltrimethylammonium acid salt, furosemide [—(C═O)—SH]thioacid, furosemide S-methyl thioester, furosemide S-cyanomethyl thioester, furosemide S-ethyl thioester, furosemide S-isoamyl thioester, furosemide S-octyl thioester, furosemide S-benzyl thioester, furosemide S-(morpholinoethyl)thioester, furosemide S-[3-(dimethylaminopropyl)]thioester, furosemide S—(N,N-diethylglycolamido)thioester, furosemide S—(N,N-dimethylglycolamido)thioester, furosemide S-pivaxetil thioester, furosemide S-propaxetil thioester, furosemide S-[methoxy(poryethyleneoxy)"_,-ethyl]thioester, furosemide [—(C═O)—S$^-$]benzyltrimethylammonium thioacid salt and furosemide [—(C═O)—S$^-$] cetyltrimethylammonium thioacid salt, metasta-stable furosemide [—(C═S)—OH] thioacid, furosemide O-methyl thioester, furosemide O-cyanomethyl thioester, furosemide O-ethyl thioester, furosemide O-isoamyl thioester, furosemide O-octyl thioester, furosemide O-benzyl thioester, furosemide O-(morpholinoethyl)thioester, furosemide O-[3-(dimethylaminopropyl)]thioester, furosemide O—(N,N-diethylglycolamido)thioester, furosemide O—(N,N-dimethylglycolamido)thioester, furosemide O-pivaxetil thioester, furosemide O-propaxetil thioester, furosemide O-Imethoxy(polyethyleneoxy)$_{n-1}$-ethyl]thioester, furosemide [—(C═S)—O$^-$]benzyl-trimethylammonium thioacid salt and furosemide [—(C═S)—O$^-$]cetyltrimethylammonium thioacid salt; furosemide thioaldehyde, furosemide [—(C═S)—SH] dithioacid, furosemide methyl dithioester, furosemide cyanomethyl dithioester, furosemide ethyl dithioester, furosemide isoamyl di-thioester, furosemide octyl dithioester, furosemide benzyl dithioester, furosemide dibenzyl-thioamide, furosemide diethyl-thioamide, furosemide morpholinoethyl dithioester, furosemide 3-(dimethylamino[rho]ropyl) dithioester, furosemide N,N-diethylglycolamido dithioester, furosemide N,N-dimethylglycolamido dithioester, furosemide pivaxetil dithioester, furosemide propaxetil dithioester, furosemide methoxy(polyethyleneoxy)$_{n-1}$ ethyl dithioester, furosemide benzyltrimethylammonium dithioacid salt and furosemide cetyltrimethylammonium dithioacid salt.

Examples of analogs of piretanide include, but are not limited to: piretanide aldehyde, piretanide methyl ester, piretanide cyanomethyl ester, piretanide benzyl ester, piretanide morpholinoethyl ester, piretanide 3-(dimethylaminopropyl) ester, piretanide N,Ndiethylglycolamide ester, piretanide diethylamide, piretanide dibenzylamide, piretanide benzylltrimethylammonium salt, piretanide cetylltrimethylammonium salt, piretanide N,N8 dimethylglycolamide ester, piretanide methoxy(polyethyleneoxy)$_{n-1}$-ethyl ester, piretanide pivaxetil ester, piretanide propaxetil ester, piretanide [—(C═O)—SH]thioacid, piretanide S-methyl thioester, piretanide S-cyanomethyl thioester, piretanide S-ethyl thioester, piretanide S-isoamyl thioester, piretanide S-octyl thioester, piretanide S-benzyl thioester, piretanide S-(morpholinoethyl)thioester, piretanide S-[3-(dimethylaminopropyl)]thioester, piretanide S—(N,N-diethylglycolamido)thioester, piretanide S—(N,N-dimethylglycolamido)thioester, piretanide S-pivaxetil thioester, piretanide S-propaxetil thioester, piretanide S-[methoxy(polyethyleneoxy)$_{n-1}$ ethyl]thioester, piretanide [—(C═O)—S$^-$] benzyltrimethylammonium thioacid salt and piretanide [—(C═O)—S$^-$] cetyltrimethylammonium thioacid salt; metastable piretanide [—(C═S)—OH]thioacid, piretanide O-methyl thioester, piretanide O-cyanomethyl thioester, piretanide O-ethyl thioester, piretanide O-isoamyl thioester, piretanide O-octyl thioester, piretanide O-benzyl thioester, piretanide O-(morpholinoethyl)thioester, piretanide O-[3-(dimethylaminopropyl)]thioester, piretanide O—(N,N-diethylglycolamido)thioester, piretanide, O—(N,N-dimethylglycolamido)thioester, piretanide O-pivaxetil thioester, piretanide O-propaxetil thioester, piretanide O-[methoxy(polyethyleneoxy)$_{n-1}$ ethyl]thioester, piretanide [—(C═S)—O$^-$]benzyltrimethylammonium thioacid salt and piretanide [—(C═S)—O$^-$] cetyltrimethylammonium thioacid salt; piretanide thioaldehyde, piretanide [—(C═S)—SH] dithioacid, piretanide methyl dithioester, piretanide cyanomethyl dithioester, piretanide ethyl dithioester, piretanide isoamyl dithioester, piretanide octyl dithioester, piretanide benzyl dithioester, piretanide dibenzylthioamide, piretanide diethyl-thioamide, piretanide morpholino ethyl dithioester, piretanide 3-(dimethylaminopropyl) dithioester, piretanide N,N-diethylglycolamido dithioester, piretanide N,N-dimethylglycolamido dithioester, piretanide pivaxetil dithioester, piretanide propaxetil dithioester, piretanide methoxytpolyethyleneoxyLrethyl dithioester, piretanide benzyl-trimethylammonium dithioacid salt and piretanide cetyltrimethylammonium dithioacid salt.

Examples of analogs of azozemide include, but are not limited to: tetrazolyl-substituted azosemides (such as methoxymethyl tetrazolyl-substituted azosemides, methylthiomethyl tetrazolyl-substituted azosemides, N-mPEG350-tetrazolyl-substituted azosemides), azosemide benzyltrimethylammonium salt, azosemide cetyltrimethylammonium 5 salt, pyridine substituted torsemide quaternary ammonium salts or the corresponding inner salts (zwitterions), methoxymethyl pyridinium torsemide salts, methylthiomethyl pyridinium torsemide salts and N-mPEG350-pyridinium torsemide salts.

In another embodiment, an analog of an inhibitor according to the invention may have a formula as described in the patent application WO2006/110187. Examples of said analogs include, but are not limited to, compounds of general formula I, II and/or III

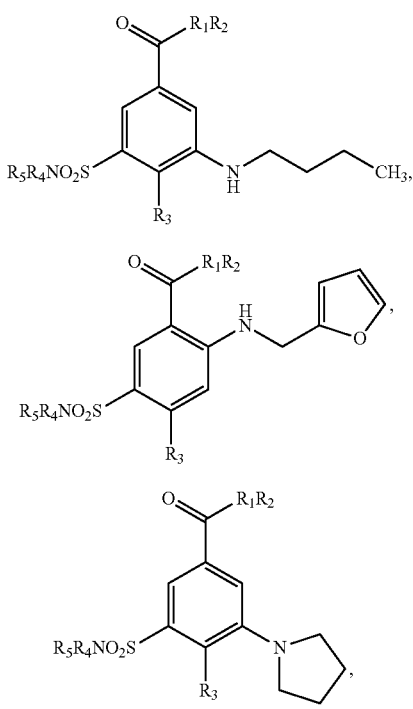

or a pharmaceutically acceptable salt, solvate, tautomer or hydrate thereof, wherein:

R1 is not present, H or O;
R2 is H or when R1 is O, is selected from the group consisting of: alkylaminodialkyl, alkylaminocarbonyldialkyl, alkyloxycarbonylalkyl, alkylaldehyde, alkylketoalkyl, alkylamide, an alkylammonium group, alkylcarboxylic acid, alkylheteroaryls, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkylalkyl and methylthioalkaryl, unsubstituted or substituted, and when R1 is not present, R2 is selected from the group consisting of: hydrogen, dialkylamino, diarylamino, dialkylaminodialkyl, dialkylcarbonylaminodialkyl, dialkylesteralkyl, dialkylaldehyde, dialkylketoalkyl, dialkylamido, dialkylcarboxylic acid, and dialkylheteroaryls, unsubstituted or substituted;
R3 is selected from the group consisting of: aryl, halo, hydroxy, alkoxy, and aryloxy, unsubstituted or substituted; and
R4 and R5 are each independently selected from the group consisting of: hydrogen, alkylaminodialkyl, alkylhydroxyaminodiakyl, unsubstituted or substituted.

Another non-limiting example of said analogs is a compound of general formula IV

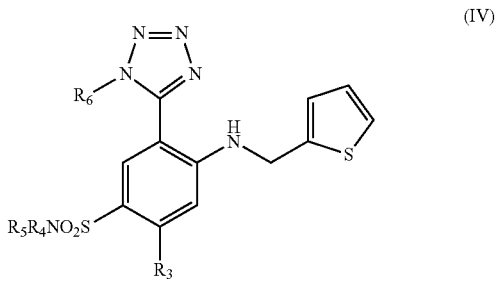

or a pharmaceutically acceptable salt, solvate, tautomer or hydrate thereof, wherein:
R3, R4 and R5 are as defined above; and
R6 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted.

Another non-limiting example of said analogs is a compound of general formula V

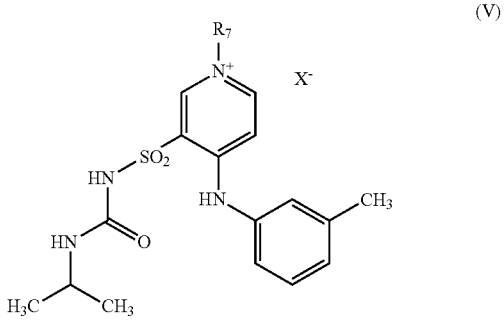

or a pharmaceutically acceptable salt, solvate, tautomer or hydrate thereof, wherein R7 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted; and $X^-$ is a halide such as bromide, chloride, fluoride, iodide or an anionic moiety such as mesylate or tosylate; alternatively, $X^-$ is not present and the compound forms an "inner" or zwitterionic salt by loss of a proton from the sulfonylurea moiety (—SO2-NH—CO—).

The term "alkyl" as used herein refers to a straight or branched chain saturated or partially unsaturated hydrocarbon radical, wherein by "unsaturated" is meant the presence of 1, 2 or 3 double or triple bonds, or a combination thereof. Examples of alkyl groups include, but are not limited to, methyl, ethyl, isopropyl, tert-butyl, N-pentyl and the like.

The term "alkylene" as used herein refers to a straight or branched chain having two terminal monovalent radical centers derived by the removal of one hydrogen atom from each of the two terminal carbon atoms of straight-chain parent alkane.

The term "aryl" as used herein refers to an aromatic group or to an optionally substituted aromatic group fused to one or more optionally substituted aromatic groups, optionally substituted with suitable substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

The term "halo" as used herein refers to bromo, chloro, fluoro or iodo. Alternatively, the term "halide" as used herein refers to bromide, chloride, fluoride or iodide.

The term "hydroxyl" as used herein refers to the group —OH.

The term "alkoxy" as used herein alone or as part of another group, refers to an alkyl group, as defined herein, appended to the parent molecular moiety through an oxy group. Representative examples of alkoxy include, but are not limited to, methoxy, ethoxy, propoxy, 2-propoxy, butoxy, tert-butoxy, pentyloxy, hexyloxy and the like.

The term "aryloxy" as used herein refers to the group —ArO wherein Ar is aryl or heteroaryl. Examples include, but are not limited to, phenoxy, benzyloxy and 2-naphthyloxy.

The term "amino" as used herein refers to —NH$_2$ in which one or both of the hydrogen atoms may optionally be replaced by alkyl or aryl or one of each, optionally substituted.

The term "alkylthio" as used herein alone or as part of another group, refers to an alkyl group, as defined herein, appended to the parent molecular moiety through a sulfur moiety. Representative examples of alkylthio include, but are not limited to, methylthio, ethylthio, N-propylthio, isopropylthio, N-butylthio, and the like.

The term "carboxy" as used herein refers to the group —CO$_2$H.

The term "quaternary ammonium" as used herein refers to a chemical structure having four bonds to the nitrogen with a positive charge on the nitrogen in the "onium" state, i.e., "R$_4$N$^+$" or "quaternary nitrogen", wherein R is an organic substituent such as alkyl or aryl. The term "quaternary ammonium salt" as used herein refers to the association of the quaternary ammonium with a cation.

The term "substituted" as used herein refers to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulf[iota]nyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, alkylamino, dialkylamino, guanidino, ureido and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent.

Another suitable substituted group is also deuterium.

The term "solvate" as used herein is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, isopropanol, ethanol, methanol, DMSO, ethyl acetate, acetic acid, or ethanolamine.

The term "hydrate" as used herein refers to the compound when the solvent is water.

In another embodiment, an analog of an inhibitor of the chloride transporter according to the invention may have a formula as described in the patent application WO2012/018635. Examples of said analogs include but are not limited to a compound of formula:

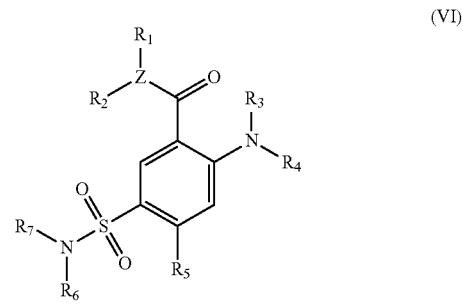

(VI)

or a pharmaceutically acceptable salt thereof, wherein:

Z is oxygen or nitrogen;

R1 and R2 are each independently hydrogen, alkyl, aryl, arylalkyl, heteroaryl, heteroaryl alkyl, heterocyclo alkyl, or R1 and R2, together with the atom to which they are attached, form a 4-7 membered heterocyclic ring that can have one or more additional heteroatoms and can have one or more substituents, with the proviso that if Z is oxygen, then R2 is not present;

R3 and R4 are each independently hydrogen, alkyl, cycloalkyl, cycloalkyl alkyl, aryl, arylalkyl, heteroaryl, or heteroarylalky, or R3 and R4, together with the atom' to which they are attached, form a 4-7 membered heterocyclic ring that can have one or more additional heteroatoms and can have one or more substituents;

R5 is halo, aryl, aryloxy, arylamino, heteroarylamino, heterocycloalkyl, heteroaryl, heteroaryloxy, heterocycloalkoxy, or alkythio; and R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents.

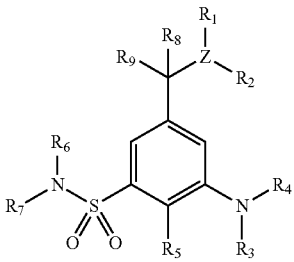

(VII)

or a pharmaceutically acceptable salt thereof, wherein:
Z is oxygen or nitrogen;
R1 and R2 are each independently hydrogen, alkyl, aryl, arylalkyl, heteroaryl, heteroarylalky], heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;
R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents;
R5 is alkoxy, halo, aryl, aryloxy, alkaryloxy, arylamino, heteroarylamino, heterocycloalkyl, heteroaryl, heteroaryloxy, heterocycloalkoxy, or alkythio;
R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents; and
R8 and R9 are each independently hydrogen, alkyl, or R8 and R9 together with the atom to which they are attached, form a 3-6 membered substituted or unsubstituted cycloalkyl or heterocycloalkyl ring.

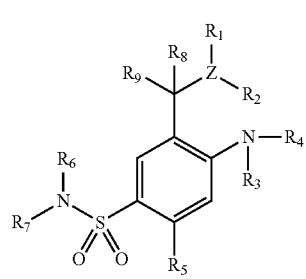

(VIII)

or a pharmaceutically acceptable salt thereof, wherein:
Z is oxygen or nitrogen;
R1 and R2 are each independently hydrogen, alkyl, aryl, arylalkyl, heteroaryl, heteroarylalkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;
R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents;
R5 is alkoxy, halo, aryl, aryloxy, alkaryloxy, arylamino, heteroarylamino, heterocycloalkyl, heteroaryl, heteroaryloxy, heterocycloalkoxy, or alkythio;
R6 nd R7 are each independently hydrogen, acyl, alkyl, cycloalkyl alky], aryl or arylalkyl, or R6 and R7, together with the atom to which they are attached, form a 4-7 membered heterocyclic ring that can have one or more additional heteroatoms and can have one or more substituents; and
R8 and R9 are each independently hydrogen, alkyl, or R8 and R9 together with the atom to which they are attached, form a 3-6 membered substituted or unsubstituted cycloalkyl or heterocycloalkyl ring.

In another embodiment, an analog of the inhibitor of the chloride transporter may have a formula as described in the patent applications incorporated herein US2007/0155729, GB2207129, in U.S. Pat. Nos. 4,247,550; 3,985,777; 7,282,519.

In another embodiment, an alternative inhibitor of NKCC activity is selected from the group comprising non-diuretic compounds: protein kinase inhibitors staurosporine and K252a, through SPAK autophosphorylation and substrate phosphorylation of the co-transporter, or the sulfhydryl agents N-ethylmaleimide (NEM) and diamide (Gagnon et al. 2006 Mol. Cell. Biol. 26(2):689-698).

Preferably, the modulator of the intracellular chloride level is bumetanide, analogs, functional derivatives and prodrugs thereof.

In another embodiment of the invention, the modulator of a chloride transporter improves the outflow of chloride from neurons, preferably through the activation of transporters involved in the outflow of chloride from neurons.

Examples of transporters involved in the outflow of chloride from neurons include, but are not limited to, KCC (wherein KCC stands for "K—Cl co-transporter"), such as, for example, KCC2. In one embodiment, said modulator of a chloride transporter is thus an activator of KCC, preferably of KCC2.

In one embodiment of the invention, the modulator improves the expression of a chloride transporter, or improves its presence on the cell surface.

In another embodiment, the modulator improves the activity of a chloride transporter, for example is an agonist of a chloride transporter or an antibody or a fragment thereof which activates the chloride transporter.

Examples of such modulators include, but are not limited to, activators of KCC, such as, for example, KCC agonists. In one embodiment, the modulator is an agonist of KCC2.

Preferably, the modulator of the intracellular chloride level is bumetanide or furosemide, more preferably bumetanide.

In one embodiment of the invention, the composition comprises a therapeutically effective amount of a modulator of intracellular chloride concentration. It corresponds to the amount of a therapeutic agent necessary and sufficient for slowing down or stopping the progression, aggravation, or deterioration of one or more symptoms of the neurodegenerative disease with Parkinsonian Syndromes; alleviating the symptoms of the neurodegenerative disease with Parkinsonian Syndromes; curing the neurodegenerative disease with Parkinsonian Syndromes.

According to the invention, the effective amount of a modulator of intracellular chloride concentration is calculated in order to reach a desired intracellular concentration of chloride.

Therefore, according to an embodiment, the effective amount of a modulator of intracellular chloride concentration corresponds to the amount to be administered to a subject in need thereof for reaching the intracellular chloride concentration measured in a healthy subject. As used herein, a "healthy subject" refers to a subject that is not affected, preferably not diagnosed, with a neurodegenerative disease with Parkinsonian Syndromes. Preferably, said healthy subject shares characteristics with the subject to be treated, such as, for example, the same age, sex, diet, weight and the like.

In one embodiment of the invention, the effective amount of a modulator ranges from about 0.01 mg to about 500 mg, from about 0.05 mg to about 100 mg, from about 0.1 mg to about 10 mg, from about 1 to 5 mg, from about 0.5 mg to about 1.5 mg.

In one embodiment of the invention, the composition for use of the invention further comprises another therapeutic agent useful for treating a neurodegenerative disease with Parkinsonian Syndromes. Examples of therapeutic agents include, but are not limited to dopamine agonists, such as, for example, bromocriptine, cabergoline, pergolide, pramipexole, fenoldopam, ropinirole, rotigotine, quinagolide and apomorphine; monoamine oxidase inhibitors, such as, for example, benmoxin, hydralazine, iproclozide, iproniazid, isocarboxazid, isoniazid, mebanazine, nialamide, octamoxin, phenelzine, pheniprazine, phenoxypropazine, pivalylbenzhydrazine, procarbazine, safrazine, caroxazone, echinopsidine, furazolidone, linezolid, tranylcypromine, brofaromine, metralindole, minaprine, moclobemide, pirlindole, toloxatone, lazabemide, pargyline, rasagiline, selegiline; or other drugs with antiparkinsonian effects other than levodopa, for example methylphenidate, anticholinergic drugs. In one embodiment, the composition for use of the invention further comprises levodopa.

The present invention also relates to a pharmaceutical composition for treating a neurodegenerative disease with Parkinsonian Syndromes in a subject in need thereof, comprising the composition for use as hereinabove described in combination with at least one pharmaceutically acceptable excipient.

The present invention also relates to a medicament for treating a neurodegenerative disease with Parkinsonian Syndromes in a subject in need thereof, comprising the composition for use as hereinabove described.

Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the composition of the invention may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

According to an embodiment, the composition for use, the pharmaceutical composition or the medicament of the invention is injected, preferably systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal and intraperitoneal injection, and perfusion. According to an embodiment, when injected, the composition for use, the pharmaceutical composition or the medicament of the invention is sterile. Methods for obtaining a sterile pharmaceutical composition include, but are not limited to, GMP synthesis (GMP stands for "Good manufacturing practice").

According to another embodiment, the composition for use, the pharmaceutical composition or the medicament of the invention is orally administered. Examples of formulations adapted to oral administration include, but are not limited to, solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, potion, drench, syrup and liquor.

Other examples of administration routes include, but are not limited to, nasal, buccal, rectal, vaginal, topical, intratracheal, endoscopic, transdermal, transmucosal, and percutaneous administration or administration using an aerosol.

In one embodiment of the invention, the composition, pharmaceutical composition or medicament of the invention may be used in conjunction with delivery systems that facilitate delivery of the agents to the central nervous system. For example, various blood brain barrier (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory.

The present invention can also relate to a prodrug of the modulator of the intracellular chloride concentration within neurons or an encapsulation of said modulator.

In one embodiment, the composition, pharmaceutical composition or medicament of the invention is a prodrug of the selective modulator of intracellular chloride concentration within neurons.

In another embodiment, the composition, pharmaceutical composition or medicament of the invention is a prodrug of the inhibitor of chloride importation within neurons.

In another embodiment, the composition, pharmaceutical composition or medicament of the invention is a prodrug of the selective inhibitor of chloride importation within neurons.

Prodrugs as described herein are capable of passage across the blood-brain barrier and may undergo hydrolysis by CNS esterases to provide the active compound.

Prodrugs provided herein may also exhibit improved bioavailability, improved aqueous solubility, improved passive intestinal absorption, improved transporter-mediated intestinal absorption, protection against accelerated metabolism, tissue-selective delivery, less (or fewer) side effects, lessened or no deleterious drug interaction with other medications, and/or passive enrichment in the target tissue.

The term "prodrug" as used herein refers to a compound that is converted under physiological conditions, by solvolysis or metabolically to a specified compound that is pharmaceutically/pharmacologically active. The "prodrug" can be a compound of the present invention that has been chemically derivatized such that it retains some, all or none of the bioactivity of its parent drug compound and is metabolized in a subject to yield the parent drug compound. The prodrug of the present invention may also be a "partial prodrug" in that the compound has been chemically derivatized such that it retains some, all or none of the bioactivity of its parent drug compound and is metabolized in a subject to yield a biologically active derivative of the compound.

Prodrugs can be formed by attachment of biocompatible polymers, such as those previously described including polyethylene glycol (PEG), to compounds of the present invention using linkages degradable under physiological conditions. See also Schacht, et al. (1997) Poly(ethylene glycol) Chemistry and Biological Applications, American Chemical Society, San Francisco, Calif. 297-315. Attachment of PEG to proteins can be employed to reduce immunogenicity and/or extend the half-life of the compounds provided herein. Any conventional PEGylation method can be employed, provided that the PEGylated agent retains at least some pharmaceutical activity.

In one embodiment, the selective inhibitor of the invention is bumetanide-PEGylated.

In one embodiment, the present invention further provides prodrugs comprising the compounds described herein. The prodrugs can be formed utilizing a hydrolyzable coupling to the compounds described herein. Ettmayer, et al. (2004) J. Med. Chem. 47(10): 2394-2404; Testa and Mayer (2003) Hydrolysis in Drug and Prodrug Metabolism: Chemistry, Biochemistry and Enzymology Wiley-Verlag Helvetica Chimica Acta, Zuerich (Chapters 1-1): 1-780.

According to one embodiment of the invention, the composition, the pharmaceutical composition or the medicament of the invention is administered at a dose determined by the skilled artisan and personally adapted to each subject.

In a special embodiment of the invention, a therapeutically effective amount of the composition, the pharmaceutical composition or the medicament of the invention is administered at least once a day, preferably twice a day, more preferably at least three times a day.

In one embodiment of the invention, the daily amount of a modulator to be administered to a subject ranges from about 0.01 mg/day to about 500 mg/day, from about 0.05 mg/day to about 100 mg/day, from about 0.1 mg/day to about 10 mg/day, from about 1 mg/day to about 5 mg/day from about 0.5 mg/day to about 1.5 mg/day.

In one embodiment of the invention, a therapeutically effective amount of the modulator is administered in a sustained-release form. In one embodiment of the invention, the composition comprises a delivery system that controls the release of the modulator. Examples of suitable carriers for sustained or delayed release include, but are not limited to, gelatin; gum Arabic; xanthane polymers; thermoplastic resins such as, for example polyvinyl halides, polyvinyl esters, polyvinylidene halides and halogenated polyolefins; elastomers such as, for example, brasiliensis, polydienes, and halogenated natural and synthetic rubbers; and flexible thermoset resins such as polyurethanes, epoxy resins; biodegradable polymers and the like.

In one embodiment of the invention, the composition, a therapeutically effective amount of the composition, the pharmaceutical composition or the medicament of the invention is administered alone.

In another embodiment of the invention, a therapeutically effective amount of the composition, the pharmaceutical composition or the medicament of the invention is administered in combination with an effective amount of one or more other active agent(s) for treating Parkinsonian Syndromes and/or an effective amount of one or more other active agent(s) for side effects enhanced by said active agent(s) and/or surgical operation.

In another embodiment of the invention, the composition, the pharmaceutical composition or the medicament of the invention is co-formulated with other active agent(s) for treating Parkinsonian Syndromes and/or an effective amount of one or more other active agent(s) for side effects enhanced by said active agent(s) and/or surgical operation.

Examples of active agents for treating Parkinsonian Syndromes include but are not limited to: L-dopa, the dopaminergic agonists (bromocriptine, pergolide, pramipexole, ropinirole, piribedil, cabergoline, apomorphine, and lisuride), COMT enzyme (tolcapone), MAO-B inhibitors (selegiline, rasagiline), anticholinergic drugs (amantadine), and surgical treatment such as deep brain stimulation.

Side effects enhanced by said active agent(s) include but are not limited to: sleep disorders, behavioral disorders (depression, anxiety), digestive/urinary disorders, and orthostatic hypotension, pain (cramp, pins and needles, and rigidity).

Examples of active agents for treating side effects include but are not limited to: mianserine, citalopram, alprazolam, thickening agents.

In one embodiment of the invention, the composition, the pharmaceutical composition or the medicament of the invention may be administered separately or in conjunction. In another embodiment of the invention, the composition, the pharmaceutical composition or the medicament of the invention may be administered prior to, concurrent to, or subsequent to the administration of other agent(s) for treating Parkinsonian Syndromes and/or an effective amount of one or more other active agent(s) for side effects enhanced by said active agent(s).

In one embodiment of the invention, the composition, the pharmaceutical composition or the medicament of the invention may be administered to a subject in period of pre-exposure and/or post-exposure with other agent(s) for treating Parkinsonian Syndromes and/or an effective amount of one or more other active agent(s) for side effects enhanced by said active agent(s).

In one embodiment, the composition for use of the invention is for preventing, reducing or alleviating the symptoms associated with a neurodegenerative disease with Parkinsonian Syndromes. In one embodiment, the alleviation or reduction of a symptom corresponds to a diminution of the number of occurrence of said symptom per day. For example, the alleviation of tremors may correspond to a decrease in the number of crisis, or the total duration of tremors per day. In another embodiment, the alleviation or reduction of said symptoms may also correspond to a decrease in the intensity of said symptom. For example, the alleviation of tremors may correspond to a decrease in the intensity of the crisis of tremors. In a preferred embodiment, the decrease or alleviation of a symptom corresponds to both a decrease in the number of occurrence of said symptom and in a decrease in the intensity of said symptom.

Examples of motor-symptoms which may be prevented, reduced and/or alleviated include, but are not limited to, tremor at rest; akinesia and rigidity, such as, for example, slowness of movements, amimia, micrographia, loss of arm swing, difficulties in walking, sensation of stiffness; joint pain, dystonia, swallowing disorders, abnormal tiredness, trembling sensation, bradykinesia, action tremor, tremors, dysarthria, dysautonomia, dysphagia, dystonia, eye apraxia, limb apraxia, myoclonus, oculo-motor tremors, night tremor.

In one embodiment, the composition for use of the invention may also be for preventing, reducing or alleviating the non-motor symptoms associated with a neurodegenerative disease with Parkinsonian Syndromes. Examples of non-motor symptoms which may be prevented, reduced and/or alleviated include, but are not limited to, autonomic dysfunction, impairment of cognitive performance, impairment of executive performances, behavioral problems, such as, for example, behavioral problems leading to dementia, sensory problems, sleep problems, emotional problems such as, for example, depression.

The skilled artisan knows how to evaluate the efficacy of a treatment of a neurodegenerative disease with Parkinsonian Syndromes, preferably to evaluate the reduction or alleviation of the non-motor symptoms associated with a neurodegenerative disease with Parkinsonian Syndromes. For example, scales exist to assess the severity of the non-motor symptoms associated with a neurodegenerative disease with Parkinsonian Syndromes. Examples of scales which may be used to assess the efficacy of the composition of the invention on the treatment of neurodegenerative disease with Parkinsonian Syndromes, preferably on non-motor symptoms include, but are not limited to, The Unified Parkinson's Disease Rating Scale (UPDRS), preferably sections I, II and VI; Neuropsychological scales such as, for example, MMS and BREF scales; Mood evaluation scales, such as, for example, Hamilton scale and MADRS scale and Quality-of-life scales, such as, for example, Goetz, CAPIT, CAPSIT, and Marconi scales.

Methods to evaluate the efficacy of a treatment of a neurodegenerative disease with Parkinsonian Syndromes, preferably to evaluate the reduction or alleviation of the motor symptoms associated with a neurodegenerative disease with Parkinsonian Syndromes. Examples of suitable methods include, but are not limited to, assessment of the presentation of a Parkinsonian Syndrome (including the presentation of one or more of the following symptoms: tremor at rest, akinesia, rigidity, depression, joint pain, dystonia, anosmia, swallowing disorders, abnormal tiredness, trembling sensation, Levodopa response . . . ); Neuroimaging; Functional cerebral imaginal by PET, DAT scan.

In one embodiment of the invention, the subject has been diagnosed with a neurodegenerative disease with Parkinsonian Syndromes since less than 10 years, 9, 8, 7, 6, 5, 4, 3 years, preferably less than 2 years, more preferably less than 1 year.

In one embodiment of the invention, the subject is at risk of developing a neurodegenerative disease with Parkinsonian Syndromes.

In one embodiment of the invention, the subject has a genetic or familial predisposition to a neurodegenerative disease with Parkinsonian Syndromes.

In one embodiment of the invention, the subject has a genetic predisposition to PD. Examples of genetic predispositions to PD include, without limitation, mutations of the PARK6 gene or mutations of the PINK1 gene. In one embodiment, the genetic predisposition is an autosomal recessive mutation. Preferably, the subject has an autosomal recessive mutation of the PARK6 gene or Pink1 gene.

In one embodiment of the invention, the subject is affected, preferably is diagnosed with an early-onset variant of PD. Preferably, said early-onset variant of PD is an autosomal recessive PARK6-linked Parkinsonism or an autosomal recessive PINK1-linked Parkinsonism.

In one embodiment of the invention, the subject presents a non-genetic predisposition to a neurodegenerative disease with Parkinsonian Syndromes. Non-genetic risk factors for developing a neurodegenerative disease with Parkinsonian Syndromes include, but are not limited to, exposure to heavy metals, such as, for example, Lead, Manganese or Copper; exposure to pesticides such as, for example, rotenone or paraquat; exposure to pollutants; exposure to herbicides such as, for example, Substance Orange; exposure to toxic substances, such as, for example, MPTP.

In one embodiment, said Parkinsonian syndrome is a degenerative Parkinsonian syndrome or an irreversible secondary Parkinsonian syndrome.

Examples of neurodegenerative diseases with Parkinsonian Syndromes include, but are not limited to, PD, progressive supranuclear palsy, multiple system atrophy, corticobasal degeneration or Lewy body dementia.

In one embodiment of the invention, the subject is a mammal and preferably a human.

In one embodiment of the invention, the subject is a female. In another embodiment of the invention, the subject is a male.

The present invention also relates to a method for treating neurodegenerative diseases with Parkinsonian Syndromes in a subject in need thereof, wherein said method comprises administering to the subject a therapeutically effective amount of a modulator of intracellular chloride concentration.

The present invention also relates to a method for preventing, reducing or alleviating the symptoms associated with a neurodegenerative disease with Parkinsonian Syndromes in a subject in need thereof, wherein said method comprises administering to the subject a therapeutically effective amount of a modulator of intracellular chloride concentration.

In one embodiment of the invention, the method of treating comprises administering to the subject the composition, the pharmaceutical composition or the medicament of the invention.

In one embodiment of the invention, the method is for treating behavioral and/or cognitive symptoms of a neurodegenerative disease with Parkinsonian Syndromes.

In another embodiment, the method of the invention is for treating synaptic symptoms/defects of a neurodegenerative disease with Parkinsonian Syndromes.

The present invention also relates to a method for treating neurodegenerative disease with Parkinsonian Syndromes by inhibiting chloride importation into neurons in a subject in need thereof, comprising administering to the subject in need thereof a therapeutically effective amount of a compound which inhibits the importation of chloride into neurons by antagonizing NKCC co-transporter.

The present invention also relates to a method for inhibiting chloride importation into neurons of a subject in need thereof affected by neurodegenerative disease with Parkinsonian Syndromes, comprising administering to the subject a therapeutically effective amount of a compound which inhibits the importation of chloride into neurons by antagonizing NKCC co-transporter.

The present invention also relates to a method for decreasing the driving force of GABA in a subject having a neurodegenerative disease with Parkinsonian Syndromes.

EXAMPLE

Figure 1:
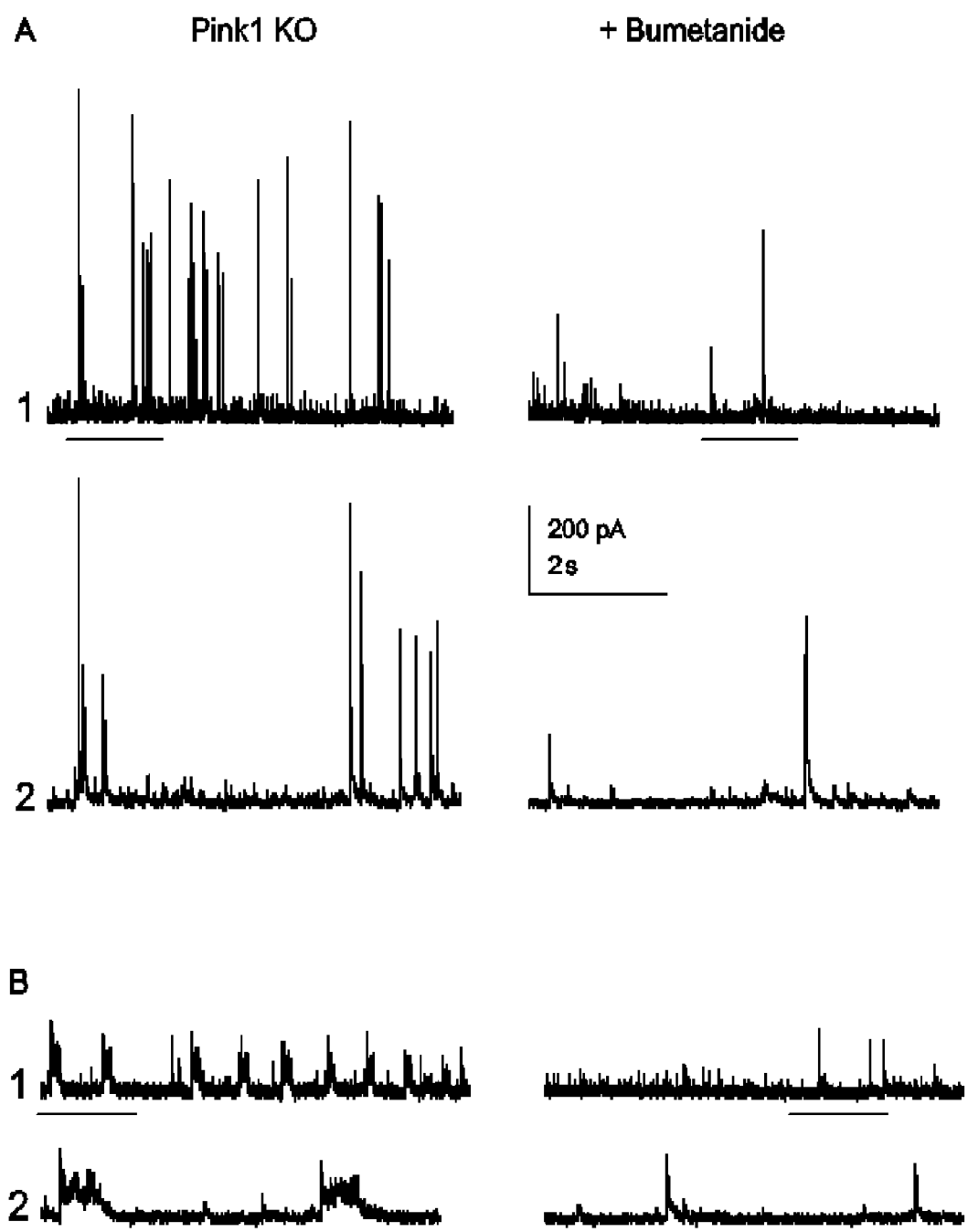
FIGS. 1A and B show voltage-clamp recordings of GABAergic spontaneous postsynaptic currents ($GABA_A$ sPSCs) in Medium Spiny Neurons (MSNs) of the striatum in Pink 1 knockout mice ($V_H$=+10 mV). The right side of these figures shows the effects of the application of bumetanide at 10 μM for 15-30 min. In A and B, the underlined portions of traces (1) are shown at a faster speed (2).

The present invention is further illustrated by the following example.

Example 1

Material

All drugs or chemicals were purchased from Sigma-Aldrich.

Methods

Animals and Surgery

Pink 1 knockout (Pink1 −/−) mouse is a genetic model of Parkinson's disease.

Pink1 −/− mutant mice of either sex at age 5-7 months were intracardially perfused with the choline solution (see below) at 4° C. and sacrificed by decapitation under halothane anesthesia. Oblique parasagittal slices (380 μm thick) were cut with an angle of 10±2° to obtain the basal ganglia slice (BGS) as described in (Beurrier et al., 2006). For the slicing procedure, the ice-cold oxygenated solution contained (in mM) 110 choline, 2.5 KCl, 1.25 $NaH_2PO_4$, 7 $MgCl_2$, 0.5 $CaCl_2$, 25 $NaHCO_3$, 7 glucose. During the recovery period, BGS were placed at room temperature with standard artificial cerebrospinal fluid (ACSF) saturated with 95% $O_2$ 5% $CO_2$ and containing (in mM): 126 NaCl, 3.5 KCl, 1.2 $NaH_2PO_4$, 1.3 $MgCl_2$, 2 $CaCl_2$, 25 $NaHCO_3$, 11 glucose.

Electrophysiology

All recordings were made at 32° C. Cells were visualized with infrared-differential interference optics (Axioskop2, Zeiss). For whole-cell voltage-clamp recordings of postsynaptic $GABA_A$ currents, the pipette (6-10 MΩ) contained (in mM): 128.5 K-gluconate, 11.5 KCl, 1 $CaCl_2$, 10 EGTA, 10 HEPES, 2.5 MgATP and 0.3 NaGTP, pH 7.32, 280 mOsm. The KGlu pipette solutions gave a reversal potential for chloride close to −63 mV at 35° C. Biocytin (Sigma, 5 mg/ml) was added to the pipette solution and osmolarity corrected when necessary. We performed patch-clamp recordings in whole cell configuration using the Digidata 1344A interface, the Multiclamp 700A amplifier and PClamp8 software (Axon Instruments, Foster City, Calif.). We identified medium spiny neurons (MSNs) during recordings based on their typical rectification during hyperpolarizing steps and their firing delay in response to depolarizing steps. MSNs were also identified by their morphological characteristics after the recording session (see immunocytochemistry). We measured spontaneous $GABA_A$ currents ($GABA_A$ sPSCs) from MSNs in voltage clamp mode at the reversal potential for glutamatergic (+10 mV) events (Cossart et al., 2000). These currents were stored on Pclamp8 (Axon Instruments, Foster City, Calif., USA) and analyzed off-line with Mini Analysis program (Synaptosoft 6.0, CA, USA), Clampfit 9.2, Origin 5.0 and Autosignal 1.7 to determine the frequency and amplitude of $GABA_A$ sPSCs. All detected currents were then visually inspected to reject artefactual events. As previously published (Dehorter et al., 2009), we defined as "giant" any single $GABA_A$ sPSC with an amplitude over 200 pA, because such sPSCs were rarely recorded in wt MSNs (on average only nine events per cell, see Results).

We defined as a burst a minimum of five sPSCs associated with a baseline elevation. More than five giant events and three bursts were required during the three min analysis for the pattern to be deemed "oscillatory". The current charge was automatically calculated by the Mini Analysis Software as the area under the curve value (taking the onset, peak and decay time points as references for each event).

Bumetanide Treatment $GABA_A$ sPSCs were recorded from identified MSNs before and during bath application of Bumetanide. Bumetanide was applied in the bath at a final concentration of 10 μM and its effect was stable after 15 min of treatment.

Statistical Analysis

For statistical comparison of data we performed paired t-tests. Error bars indicate SEM. ***P<0.001; ns (non-significant).

Results

Figure 2:
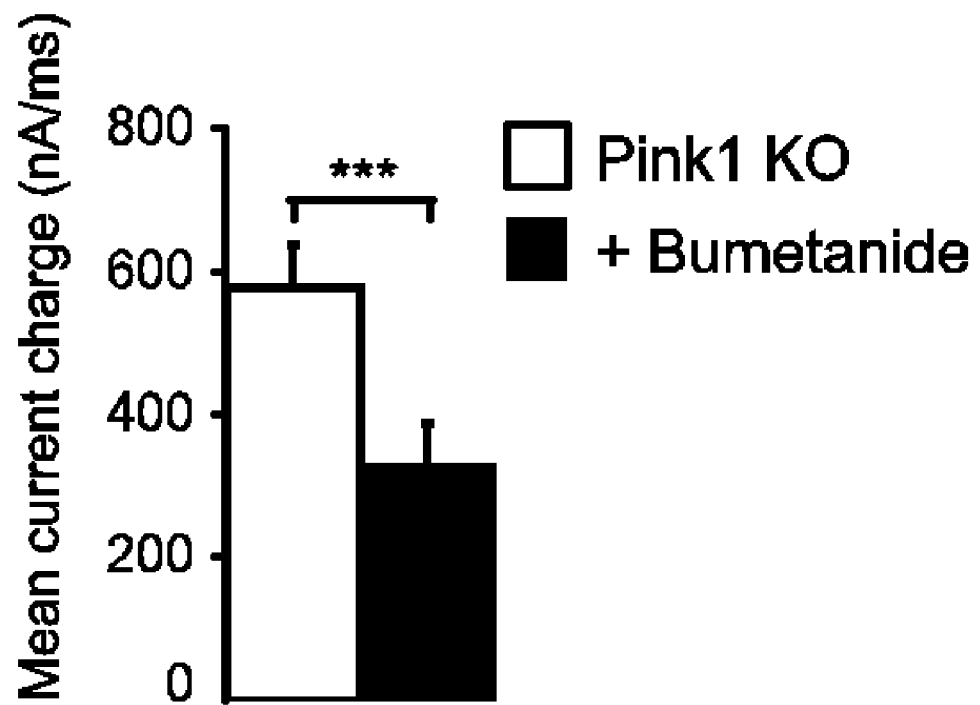
FIG. 2 is a graph illustrating the effect of bumetanide on the total current charge carried by all $GABA_A$ events.
Figure 3:
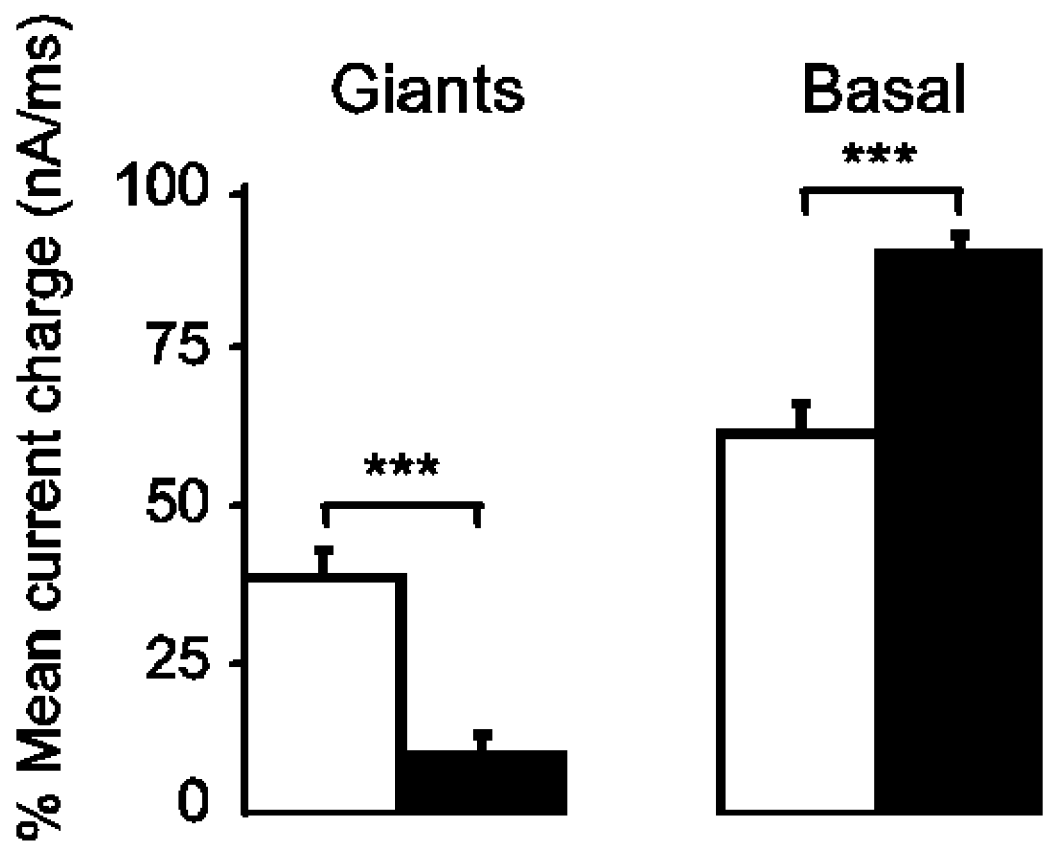
FIG. 3 is a graph showing the effect of bumetanide on the percentage of total current charge carried by giants (>200 pA) and basal $GABA_A$ events (excluding giants and bursts).
Figure 4:
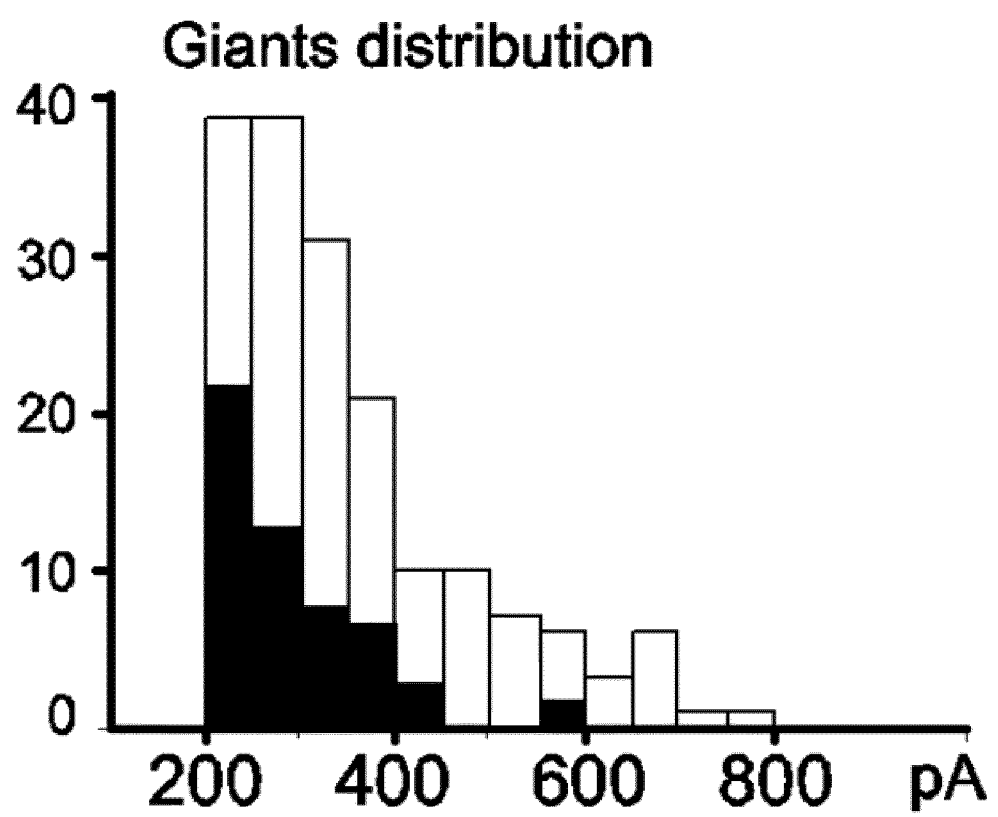
FIG. 4 is a graph showing the distribution of giant $GABA_A$ events before (white) and during (black) bumetanide application at 10 μM and for 15-30 min.

In keeping with our earlier results, Giant GABAergic currents (GGCs) were present in 50% of the MSNs from 5-7 months-old Pink1 KO mice (n=10/20). A high total current charge (566±74 nA·ms) due to the presence of the numerous GGCs occurring either singly or in bursts characterized this giant pattern, as already described (Dehorter et al., 2012). Single giant $GABA_A$ sPSCs had a high amplitude (371±31 pA; range: 201-770 pA, n=237 events) and a high frequency (0.21±0.05 Hz) (FIGS. 1A-B left). When present (n=9/10 MSNs), bursts of $GABA_A$ sPSCs had a mean intraburst frequency of 4.1±0.7 Hz and a mean amplitude of 58.6±9 pA (n=63 bursts) (FIG. 2-3 left). Giant (singly or bursting) events represented 38±5% of the total current charge. The inter GGC basal activity represented 62±5% of the total current charge (FIG. 4). In the remaining 50% of Pink1 KO MSNs (n=10/20), $GABA_A$ sPSCs had a tonic pattern as already described (Dehorter et al., 2012).

Bumetanide (10 μM), applied for 15-30 min, blocked the giant pattern that was replaced by a tonic pattern of low frequency (2.9±0.5 Hz) and low amplitude (36±4 pA) $GABA_A$ PSCs. This effect was observed in all Pink1 KO MSNs showing giant $GABA_A$ PSCs (n=10/10 MSNs). Individual giant $GABA_A$ sPSCs were still present during the three-minutes sequence analyzed (42 versus 237) but bursts totally disappeared (FIGS. 1A-B right, 2-4). Bumetanide decreased the mean total current charge by 49% to 290±70 nA·ms (P=0.0002). The few single giant $GABA_A$ sPSCs had a lower mean amplitude (338.2±22.5 pA; range, 203-593 pA; n=42 events, P=0.01) and a lower mean frequency (0.10±0.05 Hz; P=0.02) than $GABA_A$ giant sPSCs of the same MSNs before bumetanide. Giant $GABA_A$ sPSCs represented 11.7±3.9% of the total current charge (P=0.0003 compared to before bumetanide). Accordingly, the basal events between giants represented 90±3% of the total current charge (P=0.0003 compared to before bumetanide) (FIG. 3).

Spontaneous Giant currents recorded in Pink 1 knockout mice: a genetic model of parkinson disease. Voltage-clamp recordings of $GABA_A$ sPSCs with CsGlu-filled electrodes ($V_H$=+10 mV).

The results are summarized in Table 1:

|  |  | CTL | Bume |
|---|---|---|---|
| TOTAL AREA (pA · ms) | Mean | 566 | 290 |
|  | SE | 74 | 70 |
| Tonic pattern |  |  |  |
| Frequency (Hz) | Mean | 4.1 | 2.9 |
|  | SE | 0.7 | 0.5 |

-continued

|  |  | CTL | Bume |
|---|---|---|---|
| Amplitude (pA) | Mean | 58.6 | 36.0 |
|  | SE | 9.0 | 4.0 |
| Gigantic pattern |  |  |  |
| area gigantic pattern (% of the total area) | Mean | 38.3 | 11.7 |
|  | SE | 5.2 | 3.9 |
| n giants (>200 pA) | Mean | 30.8 | 5.6 |
|  | SE | 8.7 | 1.7 |
| Giants Frequency | Mean | 0.21 | 0.10 |
|  | SE | 0.05 | 0.05 |
| Giants Amplitude (pA) | Mean | 371 | 338.2 |
|  | SE | 31 | 22.5 |
| n bursts | Mean | 7.4 | 0.2 |
|  | SE | 2.0 | 0.1 |

The results that we obtained indicate that there is a unique pattern of gigantic currents in the PINK1 genetic model of Parkinson disease. This pattern is indicative and relevant to Parkinson since it is blocked by interventions that in patients with Parkinson ameliorate the syndrome and akinetic behavior (Dehorter et al J Neurosci. 2009 Jun. 17; 29(24):7776-87 & J Neurosci. 2012 Dec. 12; 32(50):18047-53). Thus, high frequency electrical stimulation of the sub-thalamic nucleus and L Dopa alleviate this pattern (Dehorter et al 2012). We also found similar excessive synchronizations in the neocortex. Therefore this pattern that is not observed in age matched recordings of naïve medium spiny neurons provides a signature of Parkinson disease. Applications of bumetanide block these gigantic currents completely suggesting that the chloride co-transporter Bumetanide—a specific inhibitor of NKCC1—is involved in their generation and its blockade will reduce the associated akinetic behavior.

Example 2

Clinical Study Patient 1

Method

A 66-year old woman, suffering from a 10-year history of Parkinson's disease was included in an open-labeled trial assessing the antiparkinsonian effects of bumetanide. She gave her informed consent to participate. The patient fulfilled the modified Queen's Square Brain Bank criteria of Parkinson's disease (Berardelli et al., 2013). She had a hypothyroidism treated by levothyroxin. Parkinson's disease was at the stage of motor fluctuation and dyskinesia. The OFF periods (bad mobility) lasted for an average of 25-50% of the awakened time. Dyskinesia was mild and intermittent. There was no marked balance impairment or cognitive decline.

Laboratory test results (potassium=3.9 mmol/l) and electrocardiography (EKG) were normal.

Antiparkinsonian treatment consisted in: L-DOPA 1,200 mg/d (7 intakes/d), ropinirole 4 mg/d, rasagiline 1 mg/d, tolcapone 300 mg/d. She also received mianserine, citalopram and alprazolam for concomitant anxiety and depression.

Bumetanide was progressively titrated up to 3 mg/d (once daily) received for a month. After having verified the good tolerability of the treatment, bumetanide was increased to 5 mg/d (once daily) and received for another month.

The patient was assessed before, 1 month and 2 months after the initiation of bumetanide. At each visit, the patient was asked about any side effects having occurred since the last visit. A Unified Parkinson's Disease Rating Scale (UPDRS) was performed before and after 2 months of treatment in the OFF stage (the patient came at 3 pm, having not taken antiparkinsonian drugs for 4 hours, and confirmed to be in her worst daily OFF stage). The antiparkinsonian treatment was unchanged during the study.

Results

No side effects were reported all along the 2 months of bumetanide treatment. Potassium at the end of the study was at 3.8 mmol/l. They were no worsening of the dyskinesia.

After 2 weeks of bumetanide received at the 5 mg/d dosage, the patient and her caregiver noticed a marked improvement of the motor condition with less severe Parkinson's disease symptoms in the OFF time and a reduction of the OFF time duration (less than 25% of the awakened time). The patient and the caregiver evaluated the overall improvement at about 30%.

The UPDRS motor severity score (III) in the OFF stage (29 after 2 months of bumetanide, the last four weeks at 5 mg/d, compared to 44 before treatment) improved by 34%. The assessment of activities of daily leaving (UPDRS II) in the worst condition improved by 40% (UPDRS II OFF=30 at baseline vs 18 at the end of the study) and was unchanged (0) in the best condition.

Conclusions

Bumetanide, received for 2 months (the last month at a dosage of 5 mg/d) was well tolerated in a patient suffering from Parkinson's disease at the stage of motor fluctuation. A marked improvement of the Parkinsonism was noticed by the patient and the caregiver. The improvement was confirmed by a 34% decrease in the UPDRS motor (III) score in the OFF stage and by a 40% decrease in the assessment of activities of daily leaving (UPDRS II) in the worst condition.

Example 3: Clinical Study Patient 2

Method

A 52-year old male, having a 8-year history of Parkinson's disease was included in an open-labeled trial assessing the antiparkinsonian effects of bumetanide. The OFF periods (bad mobility) lasted for an average of 25-50% of the awakened time.

Dyskinesia was mild and occasional (less than 25% of the awakened time). There was no marked balance impairment or cognitive decline.

Laboratory test results (potassium=4.1 mmol/1) and EKG were normal.

Antiparkinsonian treatment consisted in: L-DOPA 625 mg/day (5 intakes/day), entacapone 1,000 mg/day, ropinirole 12 mg/day.

Bumetanide: was progressively titrated up to 3 mg/day (once daily) received for a month. After having verified the good tolerability of the treatment, bumetanide was increased to 5 mg/day (once daily) and given for another month.

The patients were assessed before, 1 month and 2 months after the initiation of bumetanide. At each visit, the patient was asked about any side effects having occurred since the last visit. A Unified Parkinson's Disease Rating Scale (UPDRS) was performed before and after 2 months of treatment in a practical OFF stage (the patient came in the afternoon, having not taken antiparkinsonian drugs for 4 hours, and confirmed to be in an OFF stage). The antiparkinsonian treatment was unchanged during the study.

Results

Apart a mild pollakiuria, no side effects were reported for the entire 2 months of bumetanide treatment. Potassium at the end of the study was at 3.7 mmol/l.

The UPDRS motor severity score (III) in the OFF stage (11 after 2 months of bumetanide, the last four weeks at 5 mg/d, compared to 25 before treatment) improved by 56%. The assessment of activities of daily leaving (UPDRS II) in the worst condition improved by 33% (UPDRS II OFF=15 at baseline vs 10 at the end of the study) and was unchanged in the best condition (2 vs 3).

The invention claimed is:

1. A method for treating Parkinson's disease or associated disorders in a subject in need thereof, comprising administering to a subject in need thereof a daily therapeutically effective amount of bumetanide ranging from about 0.01 mg/day to about 100 mg/day,
wherein the associated disorder is progressive supranuclear palsy, multiple system atrophy, corticobasal degeneration or Lewy body dementia, and wherein treating does not encompass preventing.

2. The method according to claim 1, further comprising one or more active agent(s) for treating Parkinson's disease or associated disorders and/or side effects of said active agent(s).

3. The method according claim 1, wherein a therapeutically effective amount of the composition is to be administered prior to, concurrent to, or subsequent to other active agent(s) for treating Parkinson's disease or associated disorders and/or side effects of said active agent(s).

4. The method according to claim 1, wherein the subject is at risk of developing a neurodegenerative disease with Parkinsonian Syndromes.

5. The method according to claim 1, wherein the subject is diagnosed with Parkinson's disease or associated disorders.

6. The method according to claim 1, wherein the subject presents a genetic predisposition to Parkinson's disease or associated disorders.

7. The method according to claim 1, wherein the subject is affected and/or diagnosed with an early-onset variant of Parkinson's disease.

8. The method according to claim 7, wherein the early-onset variant of Parkinson's disease is an autosomal recessive PARK6-linked Parkinsonism.

9. The method according to claim 6, wherein the genetic predisposition is a mutation of the PARK6-gene.

10. The method according to claim 1, wherein the daily therapeutically effective amount of the composition to be administered to a subject, ranges from about 1 mg/day to about 5 mg/day.

11. The method according to claim 1, wherein the daily therapeutically effective amount of the composition to be administered to a subject, ranges from about 1 mg/day to about 10 mg/day.

* * * * *